(12) United States Patent
Bhuiyan et al.

(10) Patent No.: US 11,980,477 B2
(45) Date of Patent: May 14, 2024

(54) HEARING AID DETERMINING LISTENING EFFORT

(71) Applicant: Oticon A/S, Smørum (DK)

(72) Inventors: Tanveer Bhuiyan, Smørum (DK); Nicolai Westergren, Smørum (DK)

(73) Assignee: Oticon A/S, Smørum (DK)

( * ) Notice: Subject to any disclaimer, the term of this patent is extended or adjusted under 35 U.S.C. 154(b) by 135 days.

(21) Appl. No.: 17/846,664

(22) Filed: Jun. 22, 2022

(65) Prior Publication Data

US 2023/0009936 A1   Jan. 12, 2023

(30) Foreign Application Priority Data

Jul. 7, 2021   (EP) .................................. 21184232

(51) Int. Cl.
*H04R 25/00* (2006.01)
*A61B 5/00* (2006.01)

(52) U.S. Cl.
CPC .......... *A61B 5/6817* (2013.01); *H04R 25/507* (2013.01); *H04R 25/554* (2013.01); *H04R 25/70* (2013.01); *H04R 2225/41* (2013.01)

(58) Field of Classification Search
CPC .............. H04R 2225/41; H04R 25/507; H04R 25/554; H04R 25/70; H04R 25/505;
(Continued)

(56) References Cited

U.S. PATENT DOCUMENTS

| 10,827,285 | B2 | 11/2020 | Hannemann et al. | |
| 2021/0105565 | A1* | 4/2021 | Pedersen | G06N 3/08 |
| 2023/0389856 | A1* | 12/2023 | Heasman | A61B 5/369 |

FOREIGN PATENT DOCUMENTS

| WO | WO 2019/132115 A1 | 7/2019 |
| WO | WO 2021/046237 A1 | 3/2021 |

OTHER PUBLICATIONS

Bernarding et al., "Extraction of Listening Effort Correlates in the Oscillatory EEG Activity: Investigation of Different Hearing Aid Configurations", 6th Annual International IEEE EMBS Conference on Neural Engineering, 2013, pp. 1258-1261.
(Continued)

*Primary Examiner* — Phylesha Dabney
(74) *Attorney, Agent, or Firm* — Birch, Stewart, Kolasch & Birch, LLP (57) ABSTRACT

Hearing aid system comprising at least one hearing aid is provided. The hearing aid system further comprising an input unit for receiving an input sound signal from an environment of the hearing aid user and providing at least one electric input signal representing said input sound signal, an output unit for providing at least one set of stimuli perceivable as sound to the hearing aid user based on processed versions of said at least one electric input signal, a processing unit connected to said input unit and to said output unit and comprising signal processing parameters to provide said processed versions of said at least one electric input signal, at least one photoplethysmogram (PPG) sensor configured to provide a PPG signal of the hearing aid user, and a listening effort determination unit configured to provide at least one PPG morphology parameter value based at least on the PPG signal, compare the at least one PPG morphology parameter value with at least one corresponding reference PPG morphology parameter value and determine a morphology comparison measure, and determine a listening effort of the hearing aid user. A hearing aid is further provided.

20 Claims, 6 Drawing Sheets

(58) Field of Classification Search
CPC . A61B 5/6817; A61B 2562/0219; A61B 5/01; A61B 5/02108; A61B 5/02405; A61B 5/02427; A61B 5/0261; A61B 5/0816; A61B 5/1118; A61B 5/14552; A61B 5/6803; A61B 5/7267
USPC .......................................................... 381/312
See application file for complete search history.

(56) References Cited

OTHER PUBLICATIONS

European Search Report issued in priority application No. 21184232.3 dated Jan. 18, 2022.

* cited by examiner

PRIOR ART

HEARING AID DETERMINING LISTENING EFFORT

SUMMARY

The present application relates to a hearing aid system comprising at least one hearing aid. The present application further relates to a hearing aid.

The present application further relates to a method for determining a listening effort of a hearing aid user.

A Hearing Aid System

The interest of incorporating different types of physiological sensors measuring one or more physiological signals, such as electrocardiogram (ECG), photoplethysmogram (PPG), electroencephalography (EEG), etc., of a user in hearing aid systems is increasing.

However, in hearing aid systems, the application of the measurements of the physiological sensors to the audiological outcome of the hearing aids is not clear.

Listening effort has been shown to have physiological markers like pupillometry and heart parameters like PEP (pre-ejection period), but there is a lack of scientific evidence whether an ear level sensor (physiological sensors mounted in or at an ear or fully or partially implanted in the head of a user) can be used to estimate listening effort.

Further, currently, we do not take advantage of the fact that some hearing aid users have wearables with them all the time (e.g., smartwatch).

Measuring a PPG signal in the ear has been deemed the easiest solution to capture some direct vital signs e.g. heart rate (HR), heart rate variability (HRV), oxygen saturation, saturation pressure $O_2$ ($SPO_2$), respiration rate as well as some derived parameters e.g. Blood Pressure, effort etc. Most of the physiological parameters are derived based on either 1.) the PPG peak-to-peak time series signal (e.g. HR, HRV), 2.) the amplitude of the PPG signal e.g. $SPO_2$, temperature effect, and 3.) the fusion with other types of signals (electrocardiogram (ECG), accelerometer) to yield estimations like blood pressure, Pulse Transit Time (PTT).

PTT has been a useful parameter to estimate stress. It has been shown that, PTT is correlated with blood pressure and it shortens with effort.

So far, it is quite plausible to estimate listening effort based on the PTT. However, one dependency of this parameter is that, two sensors data need to be fused and time synchronization has to be ensured.

The PPG signal morphology itself contains a great deal of information. It has been shown that the change in the arterial propagation due to stiffness has proportional effect on the PPG signal morphology, hence a change in the blood pressure results in distinct changes in PPG morphology [2] [4] [5]. In other words, since any effort is manifested in the body as an increased sympathetic activation, which causes a rise in blood pressure level, such event can also be manifested on the PPG signal morphology.

Accordingly, there is a need for a new, simpler way of PPG based listening effort estimation which can enhance the accuracy of identification of difficult listening situations, and which eliminates the need for synchronizing with a contralateral hearing aid.

In an aspect of the present application, a hearing aid system is provided.

The hearing aid system may comprise at least one hearing aid. The hearing aid system may be configured to be operated based on an estimation of a listening effort of a hearing aid user.

The hearing aid may be adapted to be worn in or at an ear of a hearing aid user and/or to be fully or partially implanted in the head of the hearing aid user.

The hearing aid system may further comprise an input unit for receiving an input sound signal from an environment of the hearing aid user and for providing at least one electric input signal representing said input sound signal.

The input sound signal may comprise a speech component originating from one or more speech sound sources. The input sound signal may comprise sound comprising noise signal components. The noise signal components may arise from one or more noise sound sources. The electric input signal may represent sound in the environment of the hearing aid user.

The input unit may comprise an input transducer, e.g. a microphone, for converting the input sound signal to the electric input signal. The input unit may comprise a wireless receiver for receiving a wireless signal comprising or representing sound and for providing an electric input signal representing said sound. The wireless receiver may e.g. be configured to receive an electromagnetic signal in the radio frequency range (3 kHz to 300 GHz). The wireless receiver may e.g. be configured to receive an electromagnetic signal in a frequency range of light (e.g. infrared light 300 GHz to 430 THz, or visible light, e.g. 430 THz to 770 THz).

The hearing aid system may comprise an output unit for providing at least one set of stimuli perceivable as sound to the hearing aid user based on processed versions of said at least one electric input signal.

The hearing aid system may comprise an output unit for providing a stimulus perceived by the hearing aid user as an acoustic signal based on a processed electric signal. The output unit may comprise a number of electrodes of a cochlear implant (for a CI type hearing aid) or a vibrator of a bone conducting hearing aid. The output unit may comprise an output transducer. The output transducer may comprise a receiver (loudspeaker) for providing the stimulus as an acoustic signal to the user (e.g. in an acoustic (air conduction based) hearing aid). The output transducer may comprise a vibrator for providing the stimulus as mechanical vibration of a skull bone to the user (e.g. in a bone-attached or bone-anchored hearing aid).

The hearing aid system may comprise at least one processing unit.

The processing unit may be connected to said input unit.

The processing unit may be connected to said output unit.

The processing unit may comprise signal processing parameters of the hearing aid system to provide processed versions of said at least one electric input signal.

The hearing aid system may comprise at least one PPG sensor configured to provide a PPG signal of the hearing aid user.

A PPG sensor may provide a non-invasive monitoring of physiological parameters of the hearing aid user. A PPG sensor may be advantageous to use to monitor the heart rate of the hearing aid user.

The hearing aid system may comprise a listening effort determination unit.

The listening effort determination unit may be configured to provide at least one PPG morphology parameter value based at least on the PPG signal.

The listening effort determination unit may be configured to compare the at least one PPG morphology parameter value with at least one corresponding reference PPG morphology parameter value and determine a morphology comparison measure.

The listening effort determination unit may be configured to determine a listening effort of the hearing aid user.

Accordingly, an investigation of the PPG signal morphology is provided as a marker of listening effort to classify the easy vs difficult listening condition.

The benefit of exploiting PPG signal morphology to estimate the listening effort is quite promising and has many advantages. It requires data from only one PPG sensor. Since the analysis is independent, it relaxes the requirement of binaural synchronization (where two hearing aids are used) which is the primary requirement for the binaural Pulse-Transit-Time (Bin-PTT) determination.

The listening effort determination unit may be configured to provide a first derivative of said PPG signal (Velocity PPG signal (VPG)).

The listening effort determination unit may be configured to provide a second derivative of said PPG signal (Acceleration PPG signal (APG)).

The listening effort determination unit may be configured to provide said at least one PPG morphology parameter value based on one or more of the PPG signals, the first derivative of said PPG signal, and the second derivative of the PPG signal.

The listening effort determination unit may be configured to provide a plurality of PPG morphology parameter values.

The listening effort determination unit may be configured to compare the plurality of PPG morphology parameter values with corresponding reference PPG morphology parameter values and determine morphology comparison measures.

The listening effort determination unit may be configured to determine a listening effort of the hearing aid user.

The listening effort determination unit may be configured to determine a listening effort of the hearing aid user based on the determined morphology comparison measures.

The hearing aid system may further comprise a signal-to-noise ratio (SNR) estimator for determining a current SNR in the environment of the hearing aid user.

An SNR estimator may determine the current SNR based on processed versions (e.g. provided by a processing unit) of said at least one electric input signal.

An SNR estimator may determine the current SNR based on the at least one electric input signal from input unit.

An SNR estimator may determine the current SNR based on (e.g. processed versions of) the at least one electric input signal from at least one input transducer, such as at least one microphone, of the input unit.

The hearing aid system may be configured to adjust said signal processing parameters based on the determined listening effort.

Adjusting the signal processing parameters of the processing unit may comprise adjusting noise reduction.

Adjusting the signal processing parameters of the processing unit may comprise adjusting the gain.

Adjusting the signal processing parameters of the processing unit may comprise adjusting the directionality.

Adjusting the signal processing parameters of the processing unit may comprise adjusting the enhancement (e.g. spectral shaping).

The hearing aid system may further comprise a memory unit.

The memory unit may be configured to store the at least one corresponding reference PPG morphology parameter values.

The memory unit may be configured to store the signal processing parameters.

The memory unit may be configured to store at least one reference SNR.

For example, sets of reference SNR and reference PPG morphology parameter values may be determined based on a predetermined set of input sound signals exposed to the specific hearing aid user.

For example, the sets of reference SNR and reference PPG morphology parameter values may be determined in a calm/quiet scenario when there is no audiological challenging scenario.

Thereby, individual response on sympathetic activation may be provided.

For example, the sets of reference SNR and reference PPG morphology parameter values may be determined based on a predetermined set of input sound signals (e.g. talk and noise) exposed to a plurality of hearing aid users.

For example, the sets of reference SNR and reference PPG morphology parameter values may be determined during a fitting session.

Thereby, a fast determination of a listening effort of a hearing aid user is facilitated.

The at least one PPG morphology parameter value may comprise an amplitude at one or more fiducial points of either the PPG signal, the first derivative of said PPG signal, or the second derivative of the PPG signal.

For example, the at least one PPG morphology parameter value may be the 30% amplitude width of the systolic wave in the PPG signal.

For example, the at least one PPG morphology parameter value may be the c fiducial point amplitude in the PPG signal divided by the systolic point (S) amplitude in the PPG signal.

For example, the at least one PPG morphology parameter value may be the amplitude difference between the d and e (Dicrotic notch) fiducial points in the second derivative of the PPG signal.

For example, the at least one PPG morphology parameter value may be the amplitude difference between the d and e (Dicrotic notch) fiducial points in the first derivative of said PPG signal.

For example, the at least one PPG morphology parameter value may be the 20% amplitude width of the systolic wave in the PPG signal.

For example, the at least one PPG morphology parameter value may be the amplitude difference between the systolic point (S) and the b fiducial point in the first derivative of the PPG signal (Velocity PPG).

The at least one PPG morphology parameter value may comprise an area under a segment of either the PPG signal, the first derivative of said PPG signal, or the second derivative of the PPG signal (Acceleration PPG).

For example, the at least one PPG morphology parameter value may be the area under the O to S fiducial points in the first derivative of said PPG signal.

The at least one PPG morphology parameter value may comprise a curve area between two fiducial points of either the PPG signal, the first derivative of said PPG signal, or the second derivative of the PPG signal.

The at least one PPG morphology parameter value may comprise a time interval between two fiducial points of either the PPG signal, the first derivative of said PPG signal, or the second derivative of the PPG signal.

The at least one PPG morphology parameter value may comprise a time interval of a pulse at different heights relative to the maximum amplitude of either the PPG signal, the first derivative of said PPG signal, or the second derivative of the PPG signal.

For example, the at least one PPG morphology parameter value may be the width of the pulse at 90% height of the amplitude of the systolic wave (S).

For example, the at least one PPG morphology parameter value may be the width of the pulse at 80% height of the amplitude of the systolic wave (S).

For example, the at least one PPG morphology parameter value may be the width of the pulse at 70% height of the amplitude of the systolic wave (S).

Determining a listening effort of the hearing aid user may comprises determining whether the morphology comparison measure is within an acceptance threshold.

For example, an acceptance threshold may be either individually calibrated or based on data from a large sample of people.

Determining a listening effort of the hearing aid user may comprise determining whether, in the comparison of two or more PPG morphology parameter values with corresponding reference PPG morphology parameter values, at least one morphology comparison measure is within an acceptance threshold.

In case two or more PPG morphology parameter values are provided, said two or more PPG morphology parameter values may relate to at least two different fiducial points of the PPG signal.

In case two or more PPG morphology parameter values are provided, said two or more PPG morphology parameter values may relate to at least two different fiducial points of the first derivative of said PPG signal.

In case two or more PPG morphology parameter values are provided, said two or more PPG morphology parameter values may relate to at least two different fiducial points of the second derivative of the PPG signal.

In case two or more PPG morphology parameter values are provided, said two or more PPG morphology parameter values may relate to at least two different fiducial points of two of the PPG signal, the first derivative of said PPG signal, and/or the second derivative of the PPG signal.

The hearing aid system may comprise at least one accelerometer configured to detect a movement of the hearing aid user.

The accelerometer may be configured to detect movement in a vertical and/or in a horizontal direction. The accelerometer may be configured to detect the movement and/or acceleration and/or orientation and/or position of the hearing aid user.

The hearing aid system (e.g. the processing unit of the hearing aid system) may be configured to determine whether an activation requirement is fulfilled.

Activation requirement may refer to that one or more conditions have to be fulfilled. Accordingly, may refer to one or more thresholds, limits, boundaries, etc, have to be fulfilled before activation is determined.

The activation requirement may comprise that the movement detected by the accelerometer is below a movement threshold.

The movement threshold may refer to the accelerometer detecting no, a limited amount of movements per time unit, or only movements of a limited size/degree. Detecting movements with a limited size or amount would indicate that the hearing aid user may be standing still or at least is located in the approximate same area.

When no movement is detected, the accelerometer may move below the movement threshold. The movement threshold may be less than 200 counts/min.

For example, the hearing aid user may be standing in a room together with multiple other persons. While trying to have a conversation with one of the other persons or while trying to follow a presentation, the hearing aid user may be moving slightly around resulting in movements of limited amount per time unit or of limited size. The hearing aid user may be, however, located at the approximate same area.

The activation requirement may comprise that the current SNR is below a reference SNR.

The reference SNR may refer to the power of the signal relative to the power of the noise in the environment of the hearing aid user being at a level where the hearing aid user cannot hear another person speaking sufficiently clear and/or where the speech intelligibility is too low. The current SNR may be below the reference SNR when the current SNR is below 0 dB.

The current SNR may be below the reference SNR when the current SNR is below −5 dB.

In response to the activation requirement being fulfilled, the processing unit may be configured to activate the PPG sensor (e.g. from standby mode to operational mode).

For example, when the hearing aid user suddenly stands still (i.e. no movement is detected) to have a conversation with another person in a noisy environment (i.e. current SNR is low), then it may be required to activate the PPG sensor to determine listening effort and thus a possible required change of signal processing parameters of the hearing aid system (e.g. of the hearing aid(s)).

Thereby, power consumption of the hearing aid system may be minimized, as the activation mode (and thus power consumption) of the PPG sensor may be controlled based on the movement of the hearing aid user and of the environment the hearing aid user is in.

When the activation requirement is not fulfilled, the processing unit may be configured to change or maintain the mode of the PPG sensor to the standby mode or a deactivated mode.

A deactivated mode may refer to a shut down or power off mode. When the PPG sensor is deactivated, the power consumption of the sensor is zero.

Providing that the PPG sensor may be configured to be in a standby mode, when the activation requirement is not fulfilled, the power consumption of the sensor may be kept at a minimum, while the sensor may be rapidly changed to an operational mode immediately after the activation requirement is fulfilled. A rapid operationally functioning sensor is advantageous to provide the hearing aid user an optimal signal processing and/or to detect and/or to monitor physiological parameters of the hearing aid user when relevant.

Determining a listening effort of the hearing aid user may comprise to determine the current SNR by the SNR estimator and to compare the current SNR with the at least one reference SNR.

For example, to compare the current SNR with the at least one reference SNR may comprise to determine whether the current SNR is below a reference SNR.

The hearing aid system may further comprise an auxiliary device, said auxiliary device comprising the listening effort determination unit.

The hearing aid system may comprise two hearing aids.

Each of the two hearing aids may comprises a PPG sensor configured to provide a PPG signal of the hearing aid user.

The listening effort determination unit may be configured to determine a listening effort based on at least one of the PPG signals measured by the PPG sensors.

The listening effort determination unit may be configured to determine a listening effort based on at least one of the first derivative of said PPG signal and/or the second derivative of the PPG signal measured by the PPG sensors.

The listening effort determination unit may be configured to compare morphology comparison measures based on similar PPG morphology parameter values, which are determined by the two hearing aids.

The listening effort determination unit may be configured to determine a listening effort in case at least two morphology comparison measures based on similar PPG morphology parameter provide similar results.

Providing similar results may refer to both PPG morphology parameter values are sufficiently similar to their corresponding reference PPG morphology parameter value.

For example, a signal quality index (SQI) of each of the similar PPG morphology parameter values (determined by the two hearing aids) may be determined. The PPG morphology parameter values with the highest SQI may be chosen for determining the listening effort by the listening effort determination unit.

A Hearing Aid:

In an aspect of the present application, a hearing aid is provided.

The hearing aid may comprise an input unit for receiving an input sound signal from an environment of a hearing aid user and for providing at least one electric input signal representing said input sound signal.

The hearing aid may comprise an output unit for providing at least one set of stimuli perceivable as sound to the hearing aid user based on processed versions of said at least one electric input signal.

The hearing aid may comprise a processing unit connected to said input unit and to said output unit and comprising signal processing parameters to provide said processed versions of said at least one electric input signal.

The hearing aid may comprise at least one PPG sensor configured to provide a PPG signal of the hearing aid user.

The hearing aid may comprise a listening effort determination unit configured to provide at least one PPG morphology parameter value based at least on the PPG signal.

The hearing aid may comprise a listening effort determination unit configured to compare the at least one PPG morphology parameter value with at least one corresponding reference PPG morphology parameter value and determine a morphology comparison measure.

The hearing aid may comprise a listening effort determination unit configured to determine a listening effort of the hearing aid user.

The hearing aid may be adapted to provide a frequency dependent gain and/or a level dependent compression and/or a transposition (with or without frequency compression) of one or more frequency ranges to one or more other frequency ranges, e.g. to compensate for a hearing impairment of a user.

The hearing aid may comprise a directional microphone system adapted to spatially filter sounds from the environment, and thereby enhance a target acoustic source among a multitude of acoustic sources in the local environment of the user wearing the hearing aid. The directional system may be adapted to detect (such as adaptively detect) from which direction a particular part of the microphone signal originates. This can be achieved in various different ways as e.g. described in the prior art. In hearing aids, a microphone array beamformer is often used for spatially attenuating background noise sources. Many beamformer variants can be found in literature. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

The hearing aid may comprise antenna and transceiver circuitry (e.g. a wireless receiver) for wirelessly receiving a direct electric input signal from another device, e.g. from an entertainment device (e.g. a TV-set), a communication device, a wireless microphone, or another hearing aid. The direct electric input signal may represent or comprise an audio signal and/or a control signal and/or an information signal. The hearing aid may comprise demodulation circuitry for demodulating the received direct electric input to provide the direct electric input signal representing an audio signal and/or a control signal e.g. for setting an operational parameter (e.g. volume) and/or a processing parameter of the hearing aid. In general, a wireless link established by antenna and transceiver circuitry of the hearing aid can be of any type. The wireless link may be established between two devices, e.g. between an entertainment device (e.g. a TV) and the hearing aid, or between two hearing aids, e.g. via a third, intermediate device (e.g. a processing device, such as a remote control device, a smartphone, etc.). The wireless link may be used under power constraints, e.g. in that the hearing aid may be constituted by or comprise a portable (typically battery driven) device. The wireless link may be a link based on near-field communication, e.g. an inductive link based on an inductive coupling between antenna coils of transmitter and receiver parts. The wireless link may be based on far-field, electromagnetic radiation. The communication via the wireless link may be arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying), e.g. MSK (minimum shift keying), or QAM (quadrature amplitude modulation), etc.

The hearing aid may comprise a number of detectors configured to provide status signals relating to a current physical environment of the hearing aid (e.g. the current acoustic environment), and/or to a current state of the user wearing the hearing aid, and/or to a current state or mode of operation of the hearing aid. Alternatively, or additionally, one or more detectors may form part of an external device in communication (e.g. wirelessly) with the hearing aid. An external device may e.g. comprise another hearing aid, a remote control, and audio delivery device, a telephone (e.g. a smartphone), an external sensor, etc.

One or more of the number of detectors may operate on the full band signal (time domain).

One or more of the number of detectors may operate on band split signals ((time-) frequency domain), e.g. in a limited number of frequency bands.

The number of detectors may comprise a level detector for estimating a current level of a signal of the forward path. The detector may be configured to decide whether the current level of a signal of the forward path is above or below a given (L-)threshold value. The level detector operates on the full band signal (time domain) The level detector operates on band split signals ((time-) frequency domain).

The hearing aid may comprise a classification unit configured to classify the current situation based on input signals from (at least some of) the detectors, and possibly other inputs as well. In the present context 'a current situation' may be taken to be defined by one or more of a) the physical environment (e.g. including the current electromagnetic environment, e.g. the occurrence of electromagnetic signals (e.g. comprising audio and/or control signals) intended or not intended for reception by the hearing aid, or other properties of the current environment than acoustic);

b) the current acoustic situation (input level, feedback, etc.), and c) the current mode or state of the user (movement, temperature, cognitive load, etc.);

d) the current mode or state of the hearing aid (program selected, time elapsed since last user interaction, etc.) and/or of another device in communication with the hearing aid.

The classification unit may be based on or comprise a neural network, e.g. a trained neural network.

The hearing aid may comprise a hearing instrument, e.g. a hearing instrument adapted for being located at the ear or fully or partially in the ear canal of a user, e.g. a headset, an earphone, an ear protection device or a combination thereof. The hearing assistance system may comprise a speakerphone (comprising a number of input transducers and a number of output transducers, e.g. for use in an audio conference situation), e.g. comprising a beamformer filtering unit, e.g. providing multiple beamforming capabilities.

It is intended that some or all of the structural features of the hearing aid device described above, in the 'detailed description of embodiments' or in the claims can be included in the hearing aid. Embodiments of the hearing aid may have the same advantages as the corresponding embodiments of the hearing aid system.

Use:

In an aspect, use of a hearing aid system and a hearing aid as described above, in the 'detailed description of embodiments' and in the claims, is moreover provided. Use may be provided in a hearing aid system comprising one or more hearing aids (e.g. hearing instruments), headsets, ear phones, active ear protection systems, etc., e.g. in handsfree telephone systems, teleconferencing systems (e.g. including a speakerphone), public address systems, karaoke systems, classroom amplification systems, etc.

A Method:

In an aspect of the present application, a method for determining a listening effort of a hearing aid user is furthermore provided.

The method may comprise receiving an input sound signal from an environment of the hearing aid user and providing at least one electric input signal representing said input sound signal by an input unit.

The method may comprise providing at least one set of stimuli perceivable as sound to the hearing aid user based on processed versions of said at least one electric input signal by an output unit.

The method may comprise providing said processed versions of said at least one electric input signal by a processing unit connected to said input unit and to said output unit and comprising signal processing parameters.

The method may comprise providing a PPG signal of the hearing aid user by a PPG sensor.

The method may further comprise providing at least one PPG morphology parameter value based at least on the PPG signal.

The method may further comprise comparing the at least one PPG morphology parameter value with at least one corresponding reference PPG morphology parameter value and determining a morphology comparison measure.

The method may comprise determining a listening effort of the hearing aid user by a listening effort determination unit.

It is intended that some or all of the structural features of the hearing aid device and the hearing aid described above, in the 'detailed description of embodiments' or in the claims can be combined with embodiments of the method, when appropriately substituted by a corresponding process and vice versa. Embodiments of the method have the same advantages as the corresponding devices.

A Computer Readable Medium or Data Carrier:

In an aspect, a tangible computer-readable medium (a data carrier) storing a computer program comprising program code means (instructions) for causing a data processing system (a computer) to perform (carry out) at least some (such as a majority or all) of the (steps of the) method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Other storage media include storage in DNA (e.g. in synthesized DNA strands). Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

An Auxiliary Device:

In a further aspect, a hearing aid system comprising a hearing aid as described above, in the 'detailed description of embodiments', and in the claims, AND an auxiliary device is moreover provided.

The hearing aid system may be adapted to establish a communication link between the hearing aid and the auxiliary device to provide that information (e.g. control and status signals, possibly audio signals) can be exchanged or forwarded from one to the other.

The auxiliary device may comprise a remote control, a smartphone, or other portable or wearable electronic device, such as a smartwatch or the like.

The auxiliary device may be constituted by or comprise a remote control for controlling functionality and operation of the hearing aid(s). The function of a remote control may be implemented in a smartphone, the smartphone possibly running an APP allowing to control the functionality of the audio processing device via the smartphone (the hearing aid(s) comprising an appropriate wireless interface to the smartphone, e.g. based on Bluetooth or some other standardized or proprietary scheme).

The auxiliary device may be constituted by or comprise an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing aid.

The auxiliary device may be constituted by or comprise another hearing aid. The hearing aid system may comprise two hearing aids adapted to implement a binaural hearing system, e.g. a binaural hearing aid system.

An App:

In a further aspect, a non-transitory application, termed an APP, is furthermore provided by the present disclosure. The APP comprises executable instructions configured to be executed on an auxiliary device to implement a user interface for a hearing aid or a hearing aid system described above in the 'detailed description of embodiments', and in the claims. The APP may be configured to run on cellular phone, e.g. a smartphone, or on another portable device allowing communication with said hearing aid or said hearing aid system.

Definitions

In the present context, a hearing aid, e.g. a hearing instrument, refers to a device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing aid may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing aid may comprise a single unit or several units communicating (e.g. acoustically, electrically or optically) with each other. The loudspeaker may be arranged in a housing together with other components of the hearing aid, or may be an external unit in itself (possibly in combination with a flexible guiding element, e.g. a dome-like element).

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing aids, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit), e.g. for use in connection with an interface to a user and/or an interface to a programming device. In some hearing aids, the output unit may comprise an output transducer, such as e.g. a loudspeaker for providing an air-borne acoustic signal or a vibrator for providing a structure-borne or liquid-borne acoustic signal. In some hearing aids, the output unit may comprise one or more output electrodes for providing electric signals (e.g. to a multi-electrode array) for electrically stimulating the cochlear nerve (cochlear implant type hearing aid).

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid, e.g. through the oval window. In some hearing aids, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing aid may be adapted to a particular user's needs, e.g. a hearing impairment. A configurable signal processing circuit of the hearing aid may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing aid via an interface to a programming device (fitting system), and used by a processing algorithm executed by the configurable signal processing circuit of the hearing aid.

A 'hearing system' refers to a system comprising one or two hearing aids, and a 'binaural hearing system' refers to a system comprising two hearing aids and being adapted to cooperatively provide audible signals to both of the user's ears. Hearing systems or binaural hearing systems may further comprise one or more 'auxiliary devices', which communicate with the hearing aid(s) and affect and/or benefit from the function of the hearing aid(s). Such auxiliary devices may include at least one of a remote control, a remote microphone, an audio gateway device, an entertainment device, e.g. a music player, a wireless communication device, e.g. a mobile phone (such as a smartphone) or a tablet or another device, e.g. comprising a graphical interface. Hearing aids, hearing systems or binaural hearing systems may e.g. be used for compensating for a hearing-impaired person's loss of hearing capability, augmenting or protecting a normal-hearing person's hearing capability and/or conveying electronic audio signals to a person. Hearing aids or hearing systems may e.g. form part of or interact with public-address systems, active ear protection systems, handsfree telephone systems, car audio systems, entertainment (e.g. TV, music playing or karaoke) systems, teleconferencing systems, classroom amplification systems, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Figure 1:
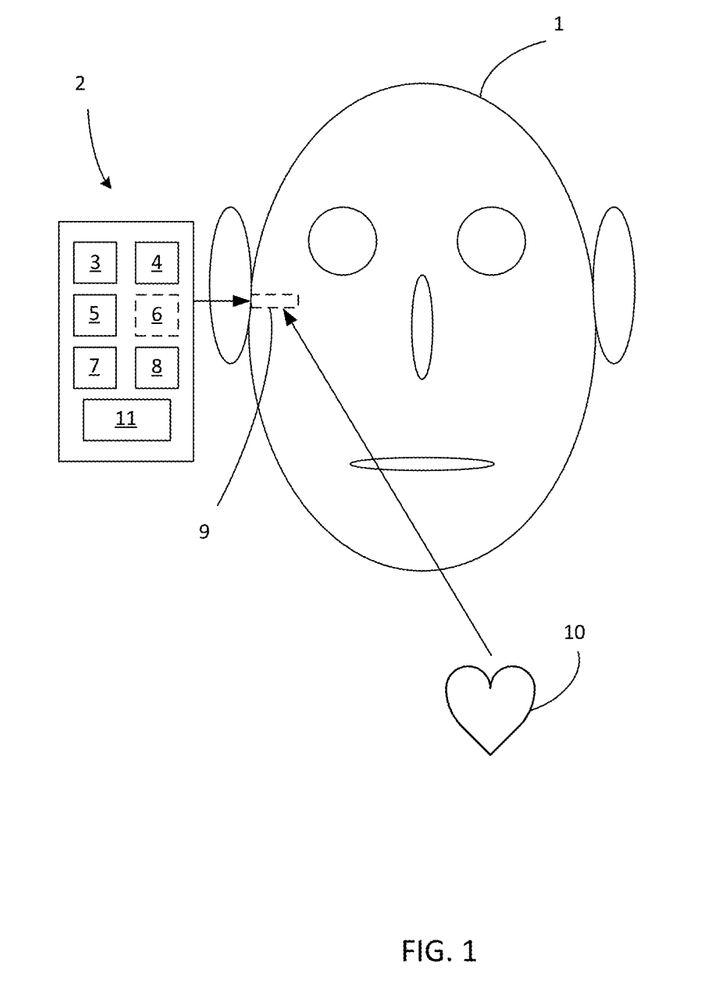
FIG. 1 shows an exemplary application scenario of a system according to the present disclosure.

FIG. 1 shows an exemplary application scenario of a system according to the present disclosure.

In FIG. 1, a hearing aid user 1 is shown. The hearing aid user 1 is wearing a hearing aid 2 at or in an ear of the hearing aid user 1 or fully or partially implanted in the head of the hearing aid user 1.

In another case, a hearing aid system may comprise the hearing aid 2. Further, a hearing aid system comprising one hearing aid in the right ear and one hearing aid in the left ear may also be contemplated.

The hearing aid 2 may comprise an input unit 3 for receiving an input sound signal from an environment of the hearing aid user 1 and provide at least one electric input signal representing said input sound signal.

The hearing aid 2 may comprise an output unit 4 for providing at least one set of stimuli perceivable as sound to the hearing aid user 1 based on processed versions of said at least one electric input signal.

The hearing aid 2 may comprise a signal processing unit 5. The signal processing unit 5 may be connected to said input unit 3 and to said output unit 4 and comprise signal processing parameters of the hearing aid 2 to provide processed versions of said at least one electric input signal.

The hearing aid 2 may comprise an SNR estimator 6 for determining an SNR in the environment of the hearing aid 2.

The hearing aid 2 may comprise a memory unit 7 configured to store at least a corresponding reference PPG morphology parameter value and/or signal processing parameters and/or at least one reference SNR of the hearing aid user 1.

In the case, where a hearing aid system comprises one hearing aid in the right ear and one hearing aid in the left ear, it is contemplated that only one or both of the hearing aids comprise a processing unit, an SNR estimator, and/or a memory unit.

The hearing aid 2 may comprise a physiological sensor such as a PPG sensor 8 configured to provide a PPG signal of the hearing aid user 1.

The PPG sensor 8 may be configured to be in contact with the skin of the ear canal 9 of the hearing aid user 1, when the hearing aid user 1 is wearing the hearing aid 2.

In the case, where a hearing aid system comprises one hearing aid in the right ear and one hearing aid in the left ear, it is contemplated that only one or both of the hearing aids comprise a PPG sensor.

In the case, where a hearing aid system comprises one hearing aid in the right ear and one hearing aid in the left ear, one or both of the hearing aids may comprise a synchronisation unit. Audio synchronization, by the synchronization units may be useful to synchronize both PPG signals measured by the two hearing aids as the sample rate for these PPG signals may be ~250 Hz.

Thus, as illustrated in FIG. 1, the hearing aid 2 may be configured to determine, by the PPG sensor 8, the heartbeat of the heart 10 of the hearing aid user 1.

The hearing aid 2 may comprise a listening effort determination unit 11.

The listening effort determination unit 11 may be configured to provide at least one PPG morphology parameter value based at least on the PPG signal measured by the PPG sensor 8. In response hereto, the listening effort determination unit 11 may compare the at least one PPG morphology parameter value with at least one corresponding reference PPG morphology parameter value stored in the memory unit 7 and determine a morphology comparison measure. Based on the morphology comparison measure, the listening effort determination unit 11 may determine a listening effort of the hearing aid user 1.

In the case, where a hearing aid system comprises one hearing aid in the right ear and one hearing aid in the left ear, each of the hearing aids may include an antenna and a transceiver circuitry for establishing a communication link (wired or wireless) to the other hearing aid, and thereby allowing the exchange of information (such as PPG signals) between the two hearing aids.

Figure 2:
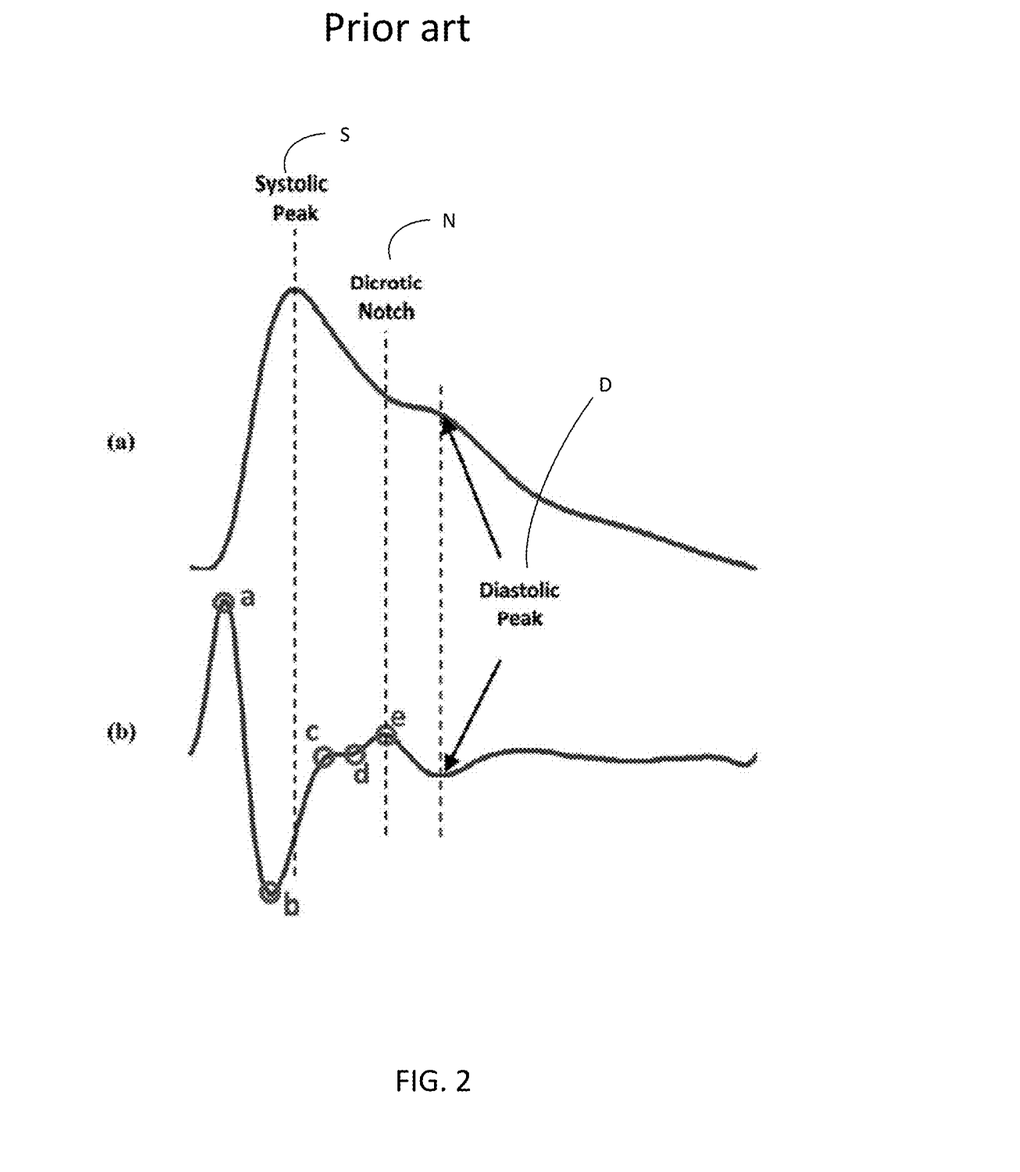
FIG. 2 shows a prior art example of a PPG signal and the second derivative of the PPG signal.

FIG. 2 shows a prior art [1] example of a PPG signal and the second derivative of the PPG signal.

The PPG signal shown in FIG. 2 is a typical PPG signal (marked a) and its second derivative (APG, marked b). As shown, three fiducial points are identified in the PPG signal. The three fiducial points are the Systolic peak (S), the Dicrotic Notch (N), and the Diastolic peak (D).

The second derivative of the PPG signal show several small components such as the c, d, and e waves, but also the a and b waves. Each of these waves give rise to a fiducial point in the form of the fiducial points a, b, c, d, and e.

Figure 3:
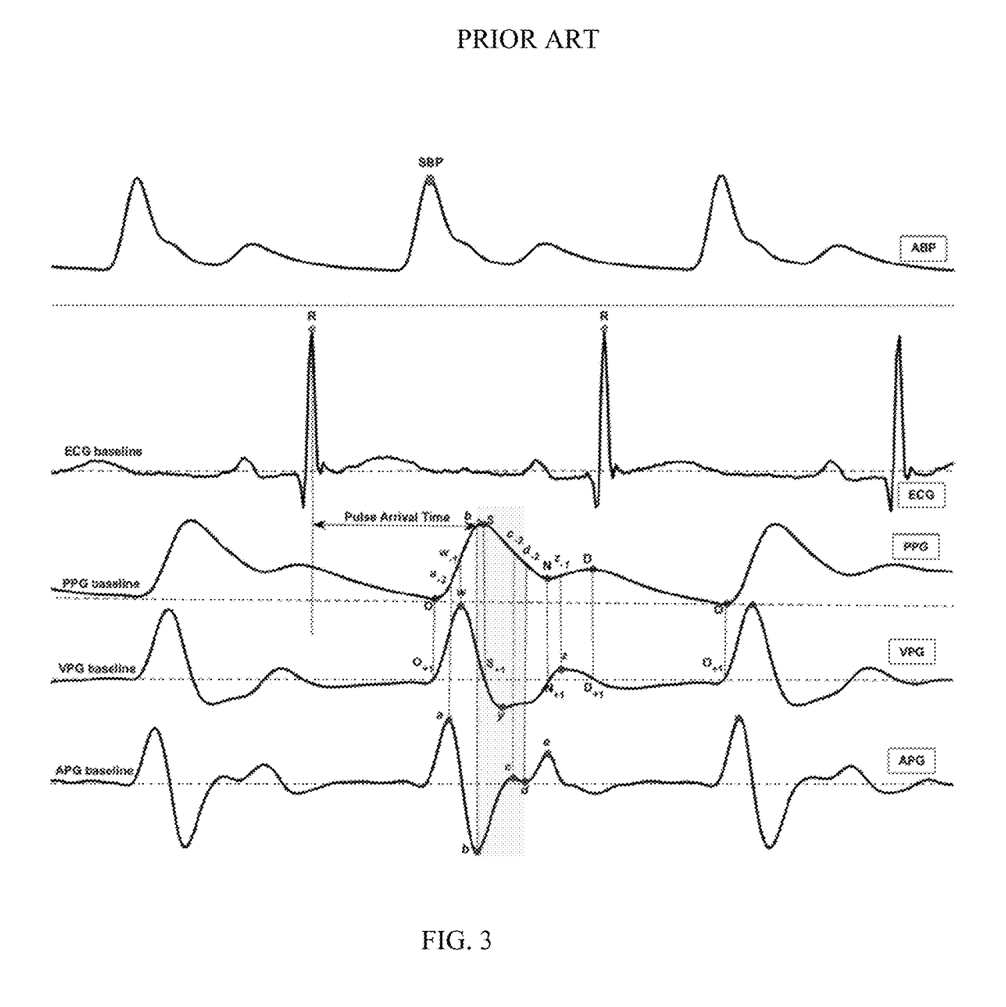
FIG. 3 shows a prior art example of a PPG signal, the first derivative of the PPG signal (VPG), and the second derivative of the PPG signal (APG).

FIG. 3 shows a prior art [2] example of a PPG signal, the first derivative of the PPG signal (VPG), and the second derivative of the PPG signal (APG). Also, the arterial blood pressure (ABP) and the electrocardiogram (ECG) waveforms are shown.

In FIG. 3, the PPG signal, the VPG, and the APG are shown on top of each other, so that the fiducial points of each of the three signal curves and their corresponding location on the other two signal curves are seen and indicated by the dotted lines.

The PPG morphology depends on the correct detection of some fiducial points in the original PPG signal, the Velocity PPG signal (VPG, 1st derivative of PPG) and the Acceleration PPG signal (APG, the 2nd derivative of PPG).

As seen, several PPG morphology features are extracted. The selection of features can be categorized as:
1) Amplitude features: Amplitude of the PPG, VPG, and/or VPG signal curves at different fiducial points
2) Area features: Area under one of the signal curves
3) Curve area: Curve area between two fiducial points on either the PPG, the VPG, and/or the VPG signal curve
4) Time feature: Time difference between two fiducial points on either the PPG, the VPG, and/or the APG signal curve
5) Pulse width: Time duration of a pulse at different heights relative to the maximum amplitude of either the PPG, the VPG, and/or the VPG signal curve The specific PPG morphology features used in the determination of listening effort of the hearing aid user are selected based on the following categories:
1. There should be a statistical significance between easy and moderately difficult (listening) conditions. To determine this, a significance test (t-test) was done between +4 dB and 0 dB, +4 dB, and −4 dB.
2. The response curve should show a symmetry between easy (+4 dB) and most difficult (−12 dB) conditions. In other words, the response curve should resemble a 'traditional' effort curve as a function of task-difficulty in the form of:

Low effort→Moderate effort→Giving up

Low response→High response→Low response

Based on the abovementioned criteria, 27 PPG morphology parameter values are selected at the 1st step.

The PPG morphology parameter values are then put through a second set of screenings. The 27 PPG morphology parameter values are then sorted according to the size of the effect between easy and difficult condition. This is done by sorting the p-values [3], providing the 10 first PPG morphology parameter values for classification between easy and difficult listening conditions. This is done with a Linear Discriminant Analysis. The 10 PPG morphology parameter values are:
1) the amplitude width at 30% height of the systolic wave (S)
2) the amplitude of the PPG signal curve at the fiducial point c divided by the amplitude of the PPG signal curve at the Systolic point (S)

3) the difference in amplitude between the fiducial points d and e in the APG signal curve
4) the difference in amplitude between the fiducial points d and e in the VPG signal curve
5) the amplitude width at 20% height of the systolic wave (S)
6) the difference in amplitude between the fiducial points S and b in the VPG signal curve
7) the width of the pulse at 90% height of the amplitude of the systolic wave (S)
8) the area under 0 to S fiducial points in VPG signal curve
9) the width of the pulse at 80% height of the amplitude of the systolic wave (S)
10) the width of the pulse at 70% height of the amplitude of the systolic wave (S)

Figure 4A:
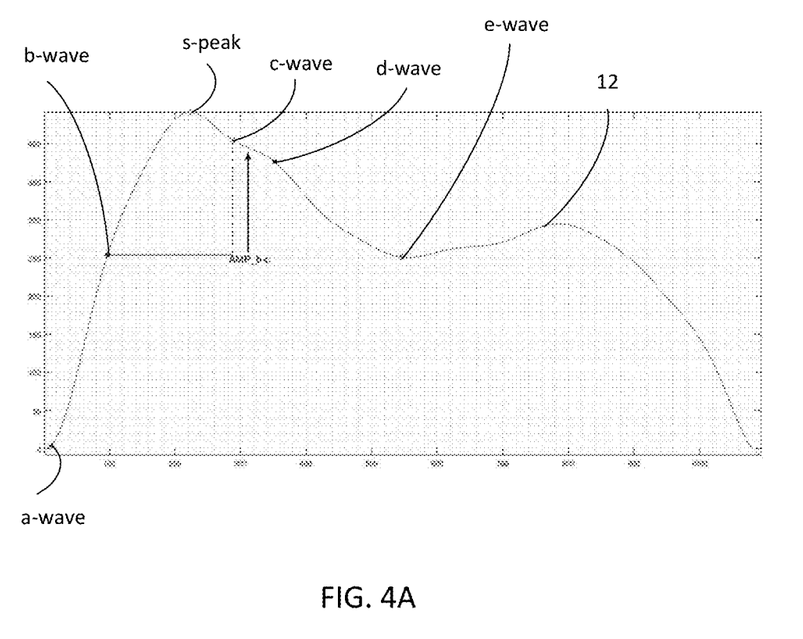
FIG. 4A shows an exemplary determination of amplitude features from the PPG signal.

FIG. 4A shows an exemplary determination of amplitude features from the PPG signal.

In FIG. 4A, a section of a PPG signal curve 12 plotted with amplitude as a function of time is shown. The fiducial points (and waves) S, a, b, c, d, and e are seen.

As an example, the difference in amplitude between the b and the c waves is determined.

Figure 4B:
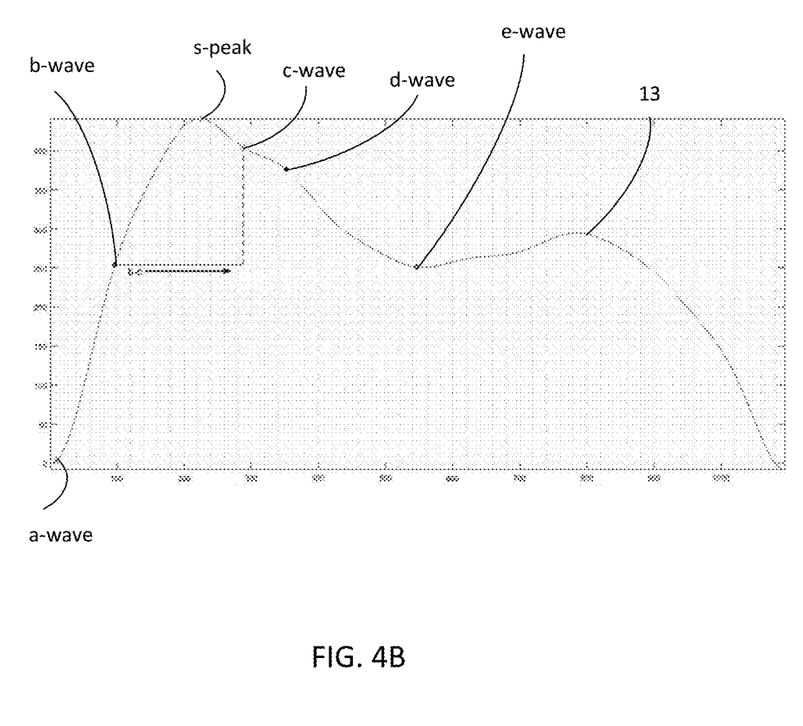
FIG. 4B shows an exemplary determination of time features from the PPG signal.

FIG. 4B shows an exemplary determination of time features from the PPG signal.

In FIG. 4B, a section of a PPG signal curve 13 plotted with amplitude as a function of time is shown. The fiducial points (and waves) S, a, b, c, d, and e are seen.

As an example, the difference in time between the b and the c fiducial points is determined.

Figure 4C:
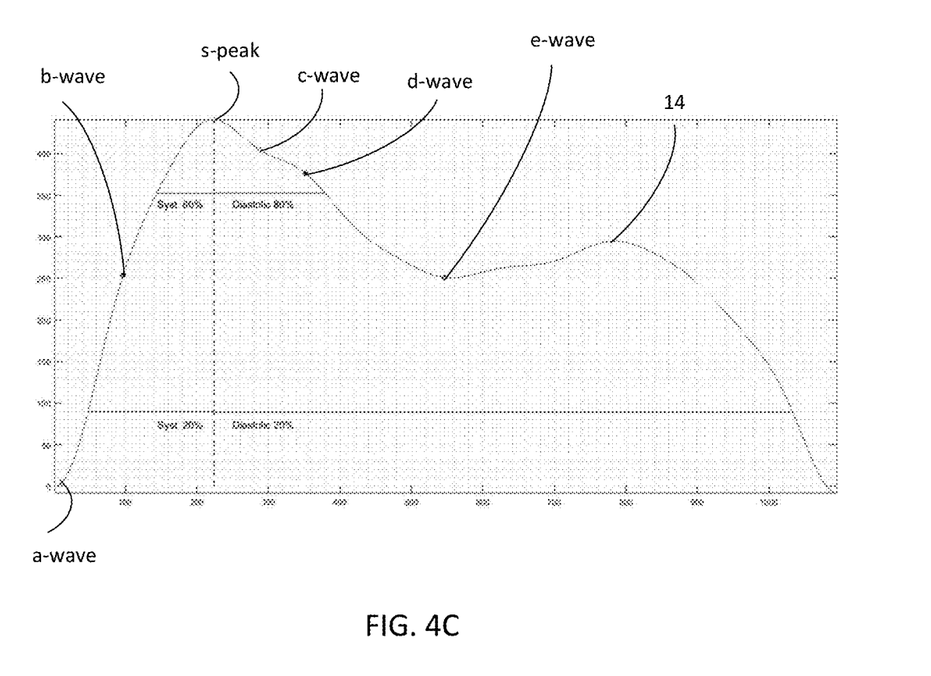
FIG. 4C shows an exemplary determination of pulse features from the PPG signal.

FIG. 4C shows an exemplary determination of pulse features from the PPG signal.

In FIG. 4C, a section of a PPG signal curve 14 plotted with amplitude as a function of time is shown. The fiducial points (and waves) S, a, b, c, d, and e are seen.

As an example, the time duration (the width) of a pulse at different heights relative to the maximum amplitude at the systolic peak (S) is determined. The different heights are shown to be 80% and 20% relative to the maximum amplitude at the systolic peak (S).

Figure 4D:
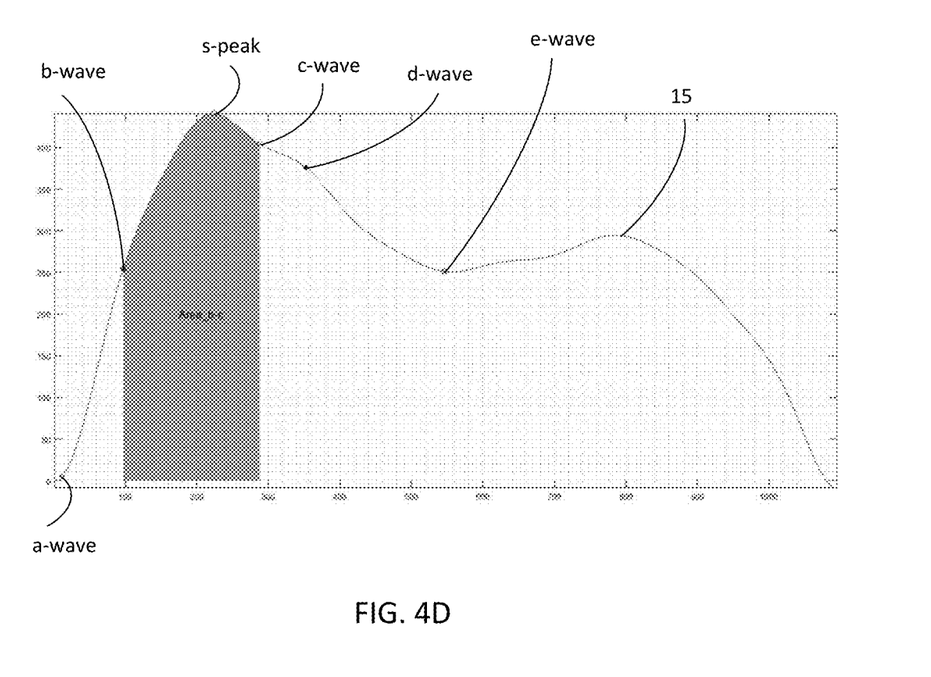
FIG. 4D shows an exemplary determination of area features from the PPG signal.

FIG. 4D shows an exemplary determination of area features from the PPG signal.

In FIG. 4D, a section of a PPG signal curve 15 plotted with amplitude as a function of time is shown. The fiducial points (and waves) S, a, b, c, d, and e are seen.

As an example, the area under the PPG signal curve 15 between the b and the c fiducial points is determined.

Figure 4E:
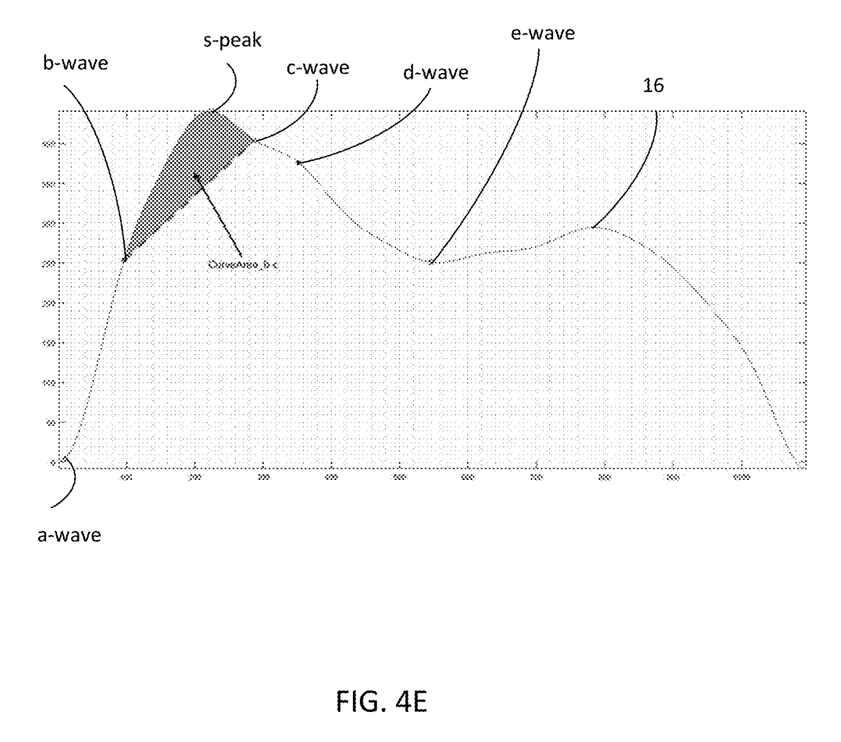
FIG. 4E shows an exemplary determination of curve area features from the PPG signal.

FIG. 4E shows an exemplary determination of curve area features from the PPG signal.

In FIG. 4E, a section of a PPG signal curve 16 plotted with amplitude as a function of time is shown. The fiducial points (and waves) S, a, b, c, d, and e are seen.

As an example, the curve area under the PPG signal curve 16 between the b and the c fiducial points is determined.

REFERENCES

[1] Elgendi, Mohamed. "Detection of c, d, and e waves in the acceleration photoplethysmogram." Computer methods and programs in biomedicine 117 2 (2013): 125-36.
[2] Y. Liang, Z. Chen, R. Ward, and M. Elgendi, "Hypertension Assessment via ECG and PPG Signals: An Evaluation Using MIMIC Database," Diagnostics, vol. 8, no. 3, September 2018, doi: 10.3390/diagnostics8030065.
[3] M. McCombe, "Intro to Feature Selection Methods for Data Science," Medium, 7 Jun. 2019. [Online]. Available: https://towardsdatascience.com/intro-to-feature-selection-methods-for-data-science-4cae2178a00a.
[4] H. Shin and S. D. Min, "Feasibility study for the non-invasive blood pressure estimation based on ppg morphology: normotensive subject study," Biomed. Eng. OnLine, vol. 16, January 2017, doi: 10.1186/s12938-016-0302-y.
[5] E. von Wowern, G. Östling, P. M. Nilsson, and P. Olofsson, "Digital Photoplethysmography for Assessment of Arterial Stiffness: Repeatability and Comparison with Applanation Tonometry," PLoS ONE, vol. 10, no. 8, August 2015, doi: 10.1371/journal.pone.0135659.

The invention claimed is:

1. Hearing aid system comprising at least one hearing aid, the hearing aid system further comprising:
   an input unit for receiving an input sound signal from an environment of the hearing aid user and for providing at least one electric input signal representing said input sound signal,
   an output unit for providing at least one set of stimuli perceivable as sound to the hearing aid user based on processed versions of said at least one electric input signal,
   a processing unit connected to said input unit and to said output unit and comprising signal processing parameters to provide said processed versions of said at least one electric input signal,
   at least one photoplethysmogram (PPG) sensor configured to provide a PPG signal of the hearing aid user, and
   a listening effort determination unit configured to:
      provide at least one PPG morphology parameter value based at least on the PPG signal,
      compare the at least one PPG morphology parameter value with at least one corresponding reference PPG morphology parameter value and determine a morphology comparison measure, and
      determine a listening effort of the hearing aid user.

2. Hearing aid system according to claim 1, wherein the listening effort determination unit is configured to provide a first derivative of said PPG signal and/or a second derivative of said PPG signal, and to provide said at least one PPG morphology parameter value based on one or more of the PPG signal, the first derivative of said PPG signal, and/or the second derivative of the PPG signal.

3. Hearing aid system according to claim 2, wherein the listening effort determination unit is configured to provide a plurality of PPG morphology parameter values, to compare the plurality of PPG morphology parameter values with corresponding reference PPG morphology parameter values and determine a morphology comparison measures, and to determine a listening effort of the hearing aid user.

4. Hearing aid system according to claim 2, wherein the hearing aid system further comprises a signal-to-noise ratio (SNR) estimator for determining a current SNR in the environment of the hearing aid user.

5. Hearing aid system according to claim 1, wherein the listening effort determination unit is configured to provide a plurality of PPG morphology parameter values, to compare the plurality of PPG morphology parameter values with corresponding reference PPG morphology parameter values and determine a morphology comparison measures, and to determine a listening effort of the hearing aid user.

6. Hearing aid system according to claim 5, wherein in case two or more PPG morphology parameter values are provided, said two or more PPG morphology parameter values relate to at least two different fiducial points of the PPG signal, the first derivative of said PPG signal, and/or the second derivative of the PPG signal.

7. Hearing aid system according to claim 5, wherein the hearing aid system further comprises a signal-to-noise ratio (SNR) estimator for determining a current SNR in the environment of the hearing aid user.

8. Hearing aid system according to claim 1, wherein the hearing aid system further comprises a signal-to-noise ratio (SNR) estimator for determining a current SNR in the environment of the hearing aid user.

9. Hearing aid system according to claim 1, wherein the hearing aid system is configured to adjust said signal processing parameters based on the determined listening effort.

10. Hearing aid system according to claim 1, wherein the hearing aid system further comprising a memory unit configured to store the at least one corresponding reference PPG morphology parameter value and/or signal processing parameters and/or at least one reference SNR.

11. Hearing aid system according to claim 10, wherein determining a listening effort of the hearing aid user comprises determining the current SNR by the SNR estimator and comparing the current SNR with the at least one reference SNR.

12. Hearing aid system according to claim 1, wherein the hearing aid system comprises at least one accelerometer configured to detect a movement of the hearing aid user.

13. Hearing aid system according to claim 1, wherein the hearing aid system further comprises an auxiliary device, said auxiliary device comprising the listening effort determination unit.

14. Hearing aid system according to claim 1, wherein the hearing aid system comprising two hearing aids, where each of the hearing aids comprises a PPG sensor configured to provide a PPG signal of the hearing aid user, and wherein the listening effort determination unit is configured to determine a listening effort based on at least one of the PPG signals measured by the PPG sensors.

15. Hearing aid system according to claim 14, wherein the listening effort determination unit is configured to compare morphology comparison measures based on similar PPG morphology parameter, which are determined from the two hearing aids, and where the listening effort determination unit is configured to determine a listening effort in case at least two morphology comparison measures based on similar PPG morphology parameter provide substantially similar results.

16. Hearing aid system according to claim 1, wherein the at least one PPG morphology parameter value comprises at least one of:
    an amplitude at one or more fiducial points of either the PPG signal, the first derivative of said PPG signal, or the second derivative of the PPG signal,
    an area under a segment of either the PPG signal, the first derivative of said PPG signal, or the second derivative of the PPG signal,
    a curve area between two fiducial points of either the PPG signal, the first derivative of said PPG signal, or the second derivative of the PPG signal,
    a time interval between two fiducial points of either the PPG signal, the first derivative of said PPG signal, or the second derivative of the PPG signal, and
    a time interval of pulse at different height relative to the maximum amplitude of either the PPG signal, the first derivative of said PPG signal, or the second derivative of the PPG signal.

17. Hearing aid system according to claim 1, wherein determining a listening effort of the hearing aid user comprises determining whether the morphology comparison measure is within an acceptance threshold.

18. Hearing aid system according to claim 1, wherein determining a listening effort of the hearing aid user comprises determining whether, in the comparison of two or more PPG morphology parameter values with corresponding reference PPG morphology parameter values, at least one morphology comparison measure is within an acceptance threshold.

19. Hearing aid comprising
    an input unit for receiving an input sound signal from an environment of a hearing aid user and providing at least one electric input signal representing said input sound signal,
    an output unit for providing at least one set of stimuli perceivable as sound to the hearing aid user based on processed versions of said at least one electric input signal,
    a processing unit connected to said input unit and to said output unit and comprising signal processing parameters to provide said processed versions of said at least one electric input signal,
    at least one PPG sensor configured to provide a PPG signal of the hearing aid user, and
    a listening effort determination unit configured to:
        provide at least one PPG morphology parameter value based at least on the PPG signal,
        compare the at least one PPG morphology parameter value with at least one corresponding reference PPG morphology parameter value and determine a morphology comparison measure, and
        determine a listening effort of the hearing aid user.

20. Method for determining a listening effort of a hearing aid user, the method comprising:
    receiving an input sound signal from an environment of the hearing aid user and providing at least one electric input signal representing said input sound signal by an input unit,
    providing at least one set of stimuli perceivable as sound to the hearing aid user based on processed versions of said at least one electric input signal by an output unit,
    providing said processed versions of said at least one electric input signal by a processing unit connected to said input unit and to said output unit and comprising signal processing parameters,
    providing a PPG signal of the hearing aid user by a PPG sensor,
    where the method further comprises:
    providing at least one PPG morphology parameter value based at least on the PPG signal,
    comparing the at least one PPG morphology parameter value with at least one corresponding reference PPG morphology parameter value and determining a morphology comparison measure, and
    determining a listening effort of the hearing aid user by a listening effort determination unit.

* * * * *